United States Patent
Prais et al.

(10) Patent No.: US 11,672,451 B2
(45) Date of Patent: Jun. 13, 2023

(54) LANCING DEVICE

(71) Applicant: Ascensia Diabetes Care Holdings AG, Basel (CH)

(72) Inventors: Eugene Prais, West Milford, NJ (US); Robert S. Sams, Pittsfield, MA (US); Simin Yao, Boonton Township, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 503 days.

(21) Appl. No.: 16/846,199

(22) Filed: Apr. 10, 2020

(65) Prior Publication Data

US 2020/0237279 A1 Jul. 30, 2020

Related U.S. Application Data

(62) Division of application No. 14/204,190, filed on Mar. 11, 2014, now Pat. No. 10,646,150.

(60) Provisional application No. 61/777,628, filed on Mar. 12, 2013.

(51) Int. Cl.
*A61B 5/151* (2006.01)
*A61B 5/15* (2006.01)

(52) U.S. Cl.
CPC ...... *A61B 5/15186* (2013.01); *A61B 5/15109* (2013.01); *A61B 5/150648* (2013.01); *A61B 5/150022* (2013.01); *A61B 5/15105* (2013.01); *A61B 5/15117* (2013.01); *A61B 5/150183* (2013.01); *A61B 5/150412* (2013.01); *A61B 5/150503* (2013.01)

(58) Field of Classification Search
None
See application file for complete search history.

(56) References Cited

U.S. PATENT DOCUMENTS

| | | | |
|---|---|---|---|
| 4,895,147 A | | 1/1990 | Bodicky |
| 5,054,499 A | * | 10/1991 | Swierczek ......... A61B 5/15144 600/583 |
| 5,201,324 A | * | 4/1993 | Swierczek ....... A61B 5/150022 600/583 |
| 5,402,798 A | * | 4/1995 | Swierczek ....... A61B 5/150412 600/583 |
| 5,505,212 A | * | 4/1996 | Keljmann ........ A61B 5/150412 600/580 |
| 5,636,640 A | * | 6/1997 | Staehlin ........... A61B 5/150419 600/577 |
| 6,379,337 B1 | | 4/2002 | Mohammad |
| 8,211,036 B2 | | 7/2012 | Schraga |
| 8,231,547 B2 | | 7/2012 | Deck |
| 8,647,357 B2 | | 2/2014 | Christensen |
| 8,795,229 B2 | * | 8/2014 | Bakhtyari-Nejad-Esfahani .......... A61B 5/153 604/116 |
| 8,828,038 B2 | | 9/2014 | Brown et al. |

(Continued)

*Primary Examiner* — Benjamin S Melhus
(74) *Attorney, Agent, or Firm* — Erise IP, P.A.

(57) ABSTRACT

A lancing device has a domed structure that can be depressed by application of a force by a user's finger so as to expose the tip of a needle. The domed structure is configured to move from a non-depressed state to a depressed state in a manner that allows for the piercing of the user's finger. The domed structure may then recoil to its original, non-depressed position upon the user ceasing to apply the force. Other embodiments of a lancing device are disclosed.

20 Claims, 10 Drawing Sheets

(56) References Cited

U.S. PATENT DOCUMENTS

| | | | |
|---|---|---|---|
| 9,380,970 B2* | 7/2016 | Christensen | A61B 5/150305 |
| 2004/0127818 A1* | 7/2004 | Roe | A61B 5/150442 |
| | | | 600/583 |
| 2005/0085839 A1* | 4/2005 | Allen | A61B 5/150068 |
| | | | 606/181 |
| 2006/0184189 A1 | 8/2006 | Olson | |
| 2007/0093863 A1* | 4/2007 | Pugh | A61B 5/150068 |
| | | | 606/181 |
| 2007/0112281 A1* | 5/2007 | Olson | A61B 5/150022 |
| | | | 600/583 |
| 2007/0112367 A1* | 5/2007 | Olson | A61B 5/150068 |
| | | | 606/181 |
| 2008/0065130 A1* | 3/2008 | Patel | A61B 5/15117 |
| | | | 606/181 |
| 2009/0299397 A1* | 12/2009 | Ruan | A61B 5/150916 |
| | | | 606/182 |
| 2010/0249819 A1* | 9/2010 | Ishikura | A61B 5/150503 |
| | | | 606/182 |
| 2010/0305599 A1* | 12/2010 | Karbowniczek | A61B 5/1513 |
| | | | 606/182 |
| 2011/0184448 A1 | 7/2011 | Brown | |
| 2012/0203083 A1 | 8/2012 | Christensen | |
| 2012/0323142 A1 | 12/2012 | Allen | |
| 2014/0276221 A1 | 9/2014 | Prais et al. | |

* cited by examiner

LANCING DEVICE

CROSS REFERENCE TO RELATED APPLICATIONS

This is a division of U.S. patent application Ser. No. 14/204,190, filed Mar. 11, 2014, now U.S. Pat. No. 10,646,150, which claims the benefit of U.S. Provisional Patent Application No. 61/777,628, filed Mar. 12, 2013, both of which are hereby incorporated by reference herein in their entireties for all purposes.

BACKGROUND

It is well known that individuals with diabetes may monitor their blood glucose levels several times per day. This is typically accomplished by piercing the skin with a lancet, commonly in the area of a finger, and then placing a blood droplet from the piercing on a test strip which is then placed in a blood glucose monitor to establish a reading.

Automatic lancing devices have become the norm. Heretofore, such devices have been cumbersome and not efficient. An ergonomically better and functionally easier device would be welcome.

SUMMARY OF THE INVENTION

Disclosed herein is an efficient and easy-to-use lancet device. In accordance with one aspect of the disclosure, the lancet device comprises a base, a needle having a tip and having a position relative to the base, and a domed surface having an aperture. The domed surface may be arranged in a first configuration relative to the base so as to create a cavity in which at least a portion of the needle resides. In addition, when a sufficient force is applied to the domed surface, the domed surface transitions from the first configuration to a second configuration in which the tip of the needle protrudes from the aperture of the domed surface.

In accordance with another aspect of the lancet device, the position of the needle relative to the base does not change during the transition of the domed surface from the first configuration to the second configuration.

In accordance with yet another aspect of the lancet device, the domed surface comprises a flexible material, and the transition from the first configuration to the second configuration includes bending the domed surface. In addition, when the force ceases to be applied, the domed surface may automatically return to the first configuration.

In accordance with still another aspect, the position of the needle relative to the base may be altered prior to the application of force to the domed surface.

In accordance with another aspect, the domed surface comprises a middle portion and an outer portion, wherein the outer portion is attached to the base, and wherein the force is applied to the middle portion of the domed surface. In addition, a user's finger may apply the force to the domed surface, and the protrusion of the tip through the aperture of the domed surface may pierce the user's finger so as to draw blood.

In accordance with another aspect, the lancet device may also comprise a main body, and an endcap extending from the main body. The base may be placed within the endcap, so that the domed surface is exposed.

In accordance with yet another aspect, a lancet device may include a base, a needle having a tip, a cartridge in which the needle resides, and a domed surface having an aperture. The cartridge may be configured so as to allow the needle to move along the axis of the needle relative to the cartridge. The domed surface may be connected to the cartridge and arranged in a first configuration relative to the base so as to create a cavity in which at least a portion of the cartridge resides. When a sufficient force is applied to the domed surface, the domed surface may transition from the first configuration to a second configuration. When the force ceases to be applied, the domed surface returns to the first configuration, and upon the domed surface returning to the first configuration, the needle may move relative to the cartridge so as to allow the tip of the needle to protrude from the aperture of the domed surface.

In accordance with still another aspect, the lancet device may include a stand that is connected to the needle and is configured to move along the axis of the needle relative to the cartridge. In addition, the lancet may include a spring, the spring arranged within the cartridge so as to cause the needle to return to a position in which the tip of the needle is not protruding through the aperture of the domed surface. The domed surface may be made of a flexible material, and the transition from the first configuration to the second configuration may include bending the domed surface.

In accordance with another aspect, the lancet device may include a base, a needle having a tip, a button having an aperture, and a flexible structure having a middle portion and an outer portion. The button may be arranged within the base so that it may move parallel to the axis of the needle, the button having a top surface that is exposed from the base. The flexible structure may be arranged relative to the button in a first configuration so as to create a cavity in which the needle resides. In addition, when a sufficient force is applied to the top surface of the button, the button may apply a force on the outer portion of the flexible structure, causing the flexible structure to transition from the first configuration to a second configuration in which the tip of the needle protrudes from the aperture of the button. The lancet device may also include a spring, the spring being arranged between the flexible surface and the button so that it will be compressed when the flexible structure is in the second configuration. In addition, the transition from the first configuration to the second configuration may include bending the flexible structure.

In accordance with another aspect, a user's finger applies the force to the top surface of the button, and the protrusion of the tip through the aperture of the button pierces the user's finger so as to draw blood.

BRIEF DESCRIPTION OF THE DRAWINGS

The present invention will be readily understood by one skilled in the art by reviewing the following detailed description in conjunction with the accompanying drawings, wherein like reference numerals designate like structural elements, and in which.

DETAILED DESCRIPTION OF THE INVENTION

The following description of the exemplary embodiments of the invention along with the accompanying figures is presented by way of illustration and to facilitate an understanding of the disclosed system. The description is neither intended to be exhaustive nor meant to limit the scope of the invention in any manner. Accordingly, many modifications and variations are possible in light of the disclosure.

Furthermore, the features and advantages described herein are not all-inclusive and, in particular, many additional features and advantages will be apparent to one of ordinary skill in the art in view of the drawings, specification, and claims. As will also be appreciated, the invention is capable of other and different embodiments, and its several details are capable of modifications in various respects without departing from the spirit and scope of the invention.

Figure 1:
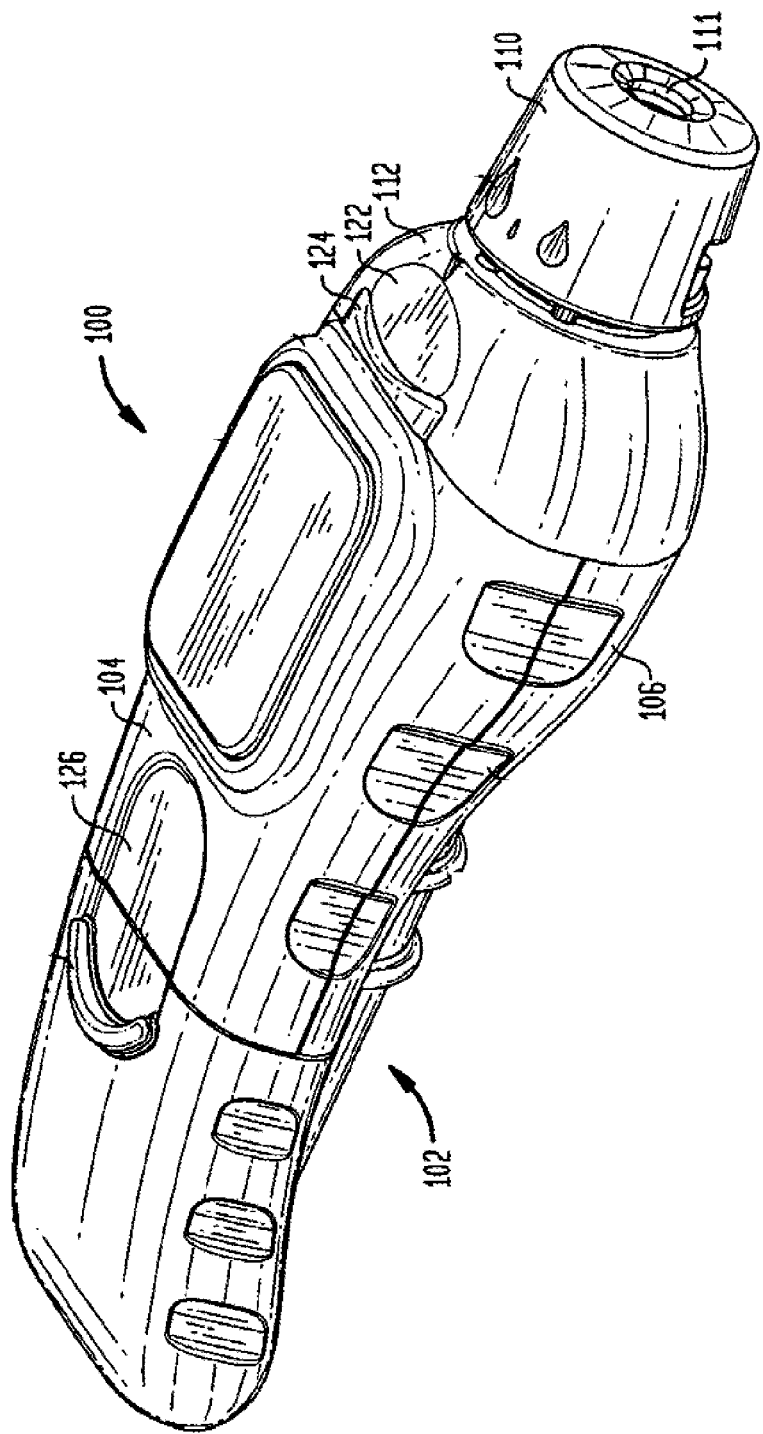
FIG. 1 is a perspective view of a lancing device in accordance with a first embodiment of the present invention, where the lancing device includes an adjustable endcap.

Referring to FIG. 1, a perspective view of lancing device 100, which may include a main body 102 configured from an upper portion 104 and a lower portion 106 mated to the upper portion. The lancet device 100 may further include an endcap 110 mounted to the upper and lower portions 104, 106 by endcap shoulders 112.

The lancet device 100 may also include a depression 122 and associated tab 124 that are incorporated with the endcap 110, and more specifically the endcap shoulders 112. The depression 122 and tab 124 may be utilized to assist with removal of the endcap from the main body 102 of the lancet device by being suited for tactical and functional recognition by human fingers.

Figure 2:
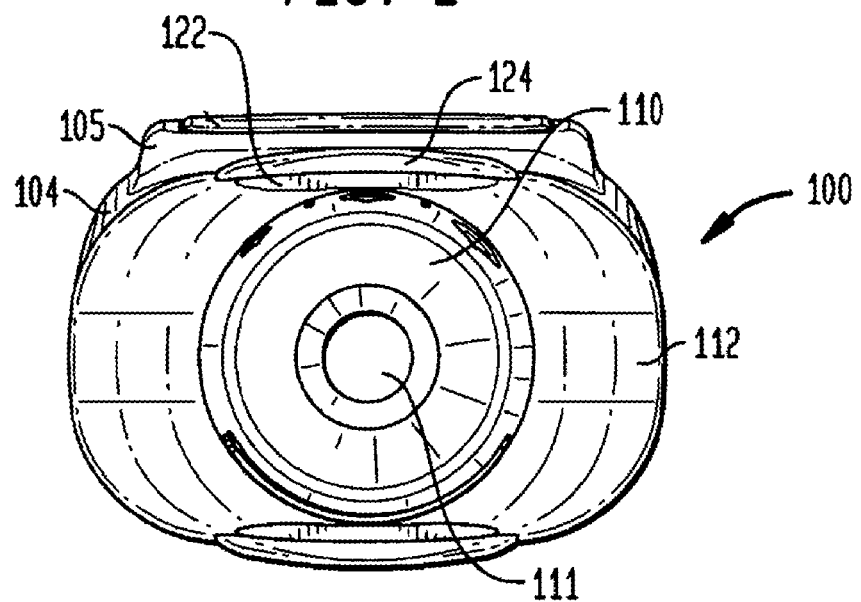
FIG. 2 is a frontal view of the lancing device of FIG. 1.
Figure 3:
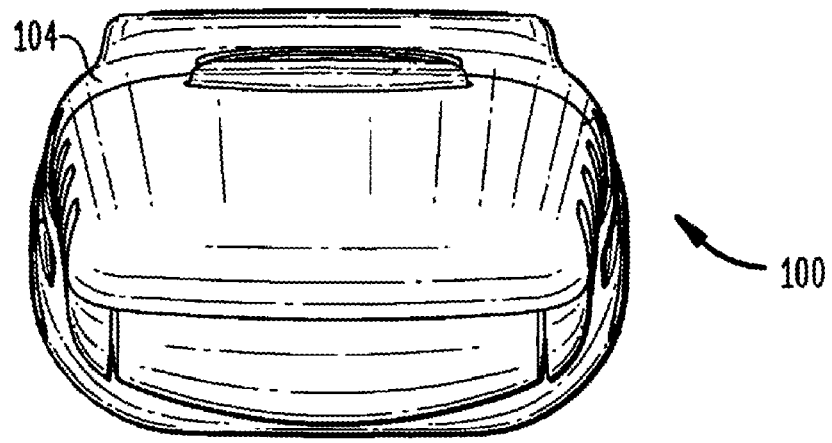
FIG. 3 is a rear view of the lancing device of FIG. 1.

FIGS. 2-3 depict additional views of the exemplary lancet device. Specifically, FIG. 2 depicts a frontal view of the exemplary lancing device and FIG. 3 depicts a rear view of the exemplary lancing device.

Figure 4:
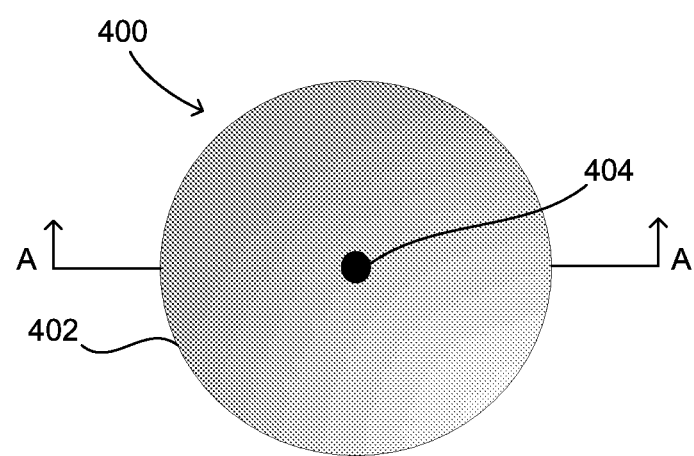
FIG. 4 is a top view of a lancet assembly in accordance with one aspect of the disclosure.
Figure 5:
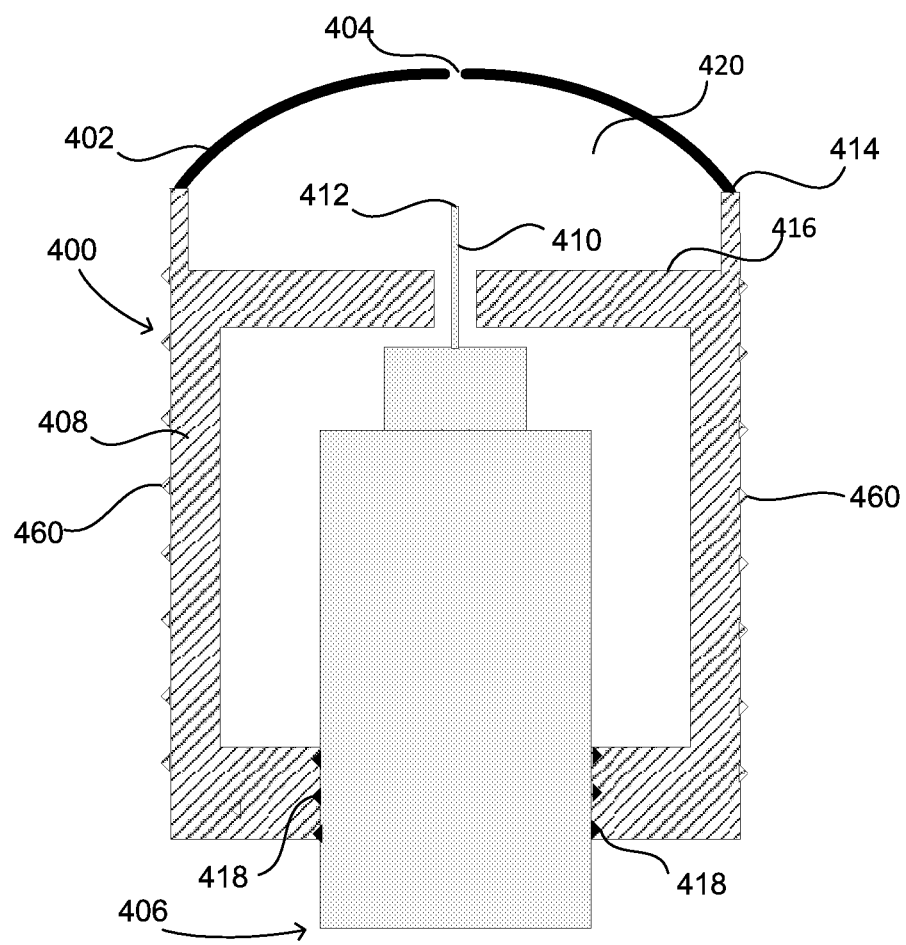
FIG. 5 is a cross-sectional view of the lancet assembly.

Moving to FIGS. 4 and 5, a lancet assembly 400 in accordance with one embodiment of the disclosure is shown. Lancet assembly 400 may be adjustably positioned within opening 111 of endcap 110 so as to be used together with lancing device 100. Specifically, FIG. 4 provides a top view of lancet assembly 400, which includes a snap lid 402 having an aperture 404. FIG. 5 provides a cross-sectional view of lancet assembly 400 from perspective A shown in FIG. 4. As seen in FIG. 5, lancet assembly 400 includes a lancet 406 and a base 408. Lancet 406 contains a needle 410, having a tip 412. Base 408 may include top surfaces 414 and 416, and snap lid 402 may be attached to one of the top surfaces, such as top surface 414. Lancet 406 may be adjustably positioned within base 408 so as to allow needle 410 to be positioned relative to top surface 416 and snap lid 402. For example, lancet 406 may contain threads 418 that allow lancet 406 to be screwed into base 408, and thereby allowing the position of lancet 406 to be adjusted within base 408. In addition, base 408 may contain threads 460 that allow base 408 to be adjustably positioned within opening 111 of endcap 110.

Figure 6:
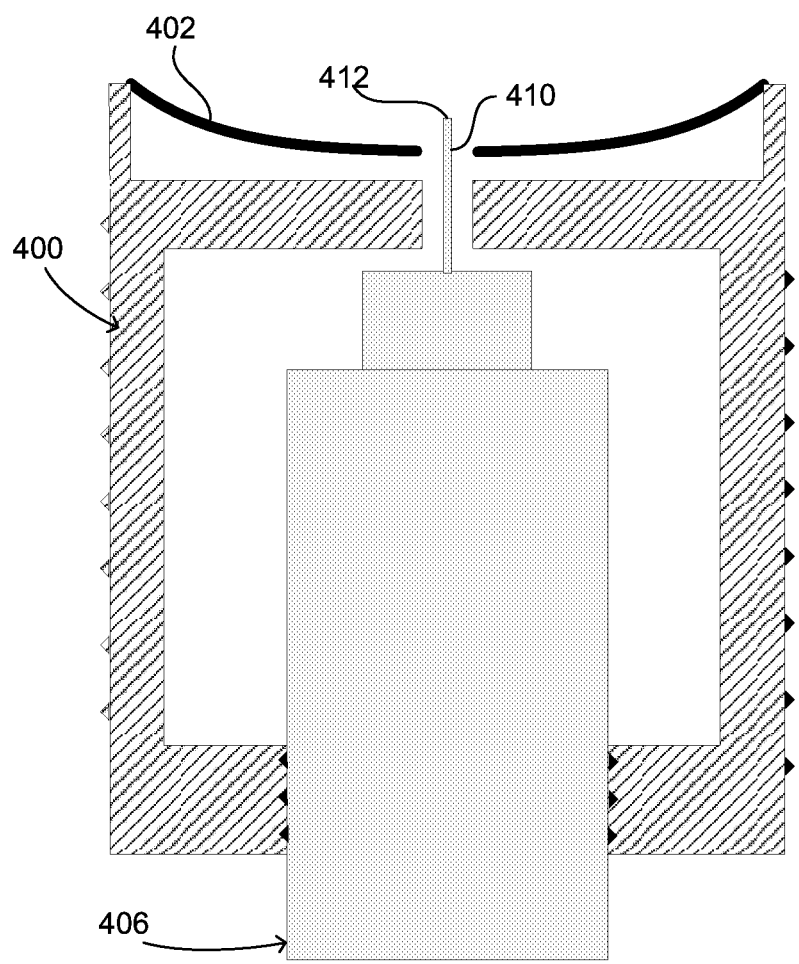
FIG. 6 is a cross-sectional view of the lancet in accordance with one aspect of the disclosure.

Lancet assembly 400 may be configured so that snap lid 402 creates a cavity 420 in which needle 410 resides. However, a user may depress snap lid 402 toward needle 410, thereby exposing tip 412 of needle 410 through aperture 404. For example, a user may press snap lid 402 using a finger (not shown) so that snap lid 402 goes from a non-depressed position shown in FIG. 5 to a depressed position shown in FIG. 6. As seen in FIG. 6, once snap lid 402 is depressed, tip 412 is exposed through aperture 404, and the user's finger will be pierced by tip 412 so as to draw a blood sample.

In accordance with one embodiment, snap lid 402 is designed to quickly move from a non-depressed position to a depressed position, allowing for a fast and clean piercing of the user's finger. In accordance with this embodiment, snap lid 402 may be in a stable state while residing in the non-depressed position. In particular, snap lid 402 may be designed so that it will not move, or will only move slightly, when a force is applied by the user, provided that the force is below a particular threshold. Once the user provides a force at or above the particular threshold value, snap lid 402 will quickly move from the non-depressed position shown in FIG. 5 to the depressed position shown in FIG. 6, allowing the user's finger to be pierced by tip 412. The user will then remove the force that was applied to snap lid 402, thereby allowing snap lid 402 to return to the non-depressed position.

Snap lid 402 may consist of any material that would allow it to move, given a predetermined amount of force, between the depressed and non-depressed positions under the desired threshold force, including any number of metals or plastics. While FIG. 4 shows snap lid 402 to be circular, snap lid 402 may take any shape that allows it move from the stable non-depressed position to the depressed position, given the application of sufficient force. For example, snap lid 402, when viewed from the perspective shown in FIG. 4, may have any shape that is desirable, including a square, oval, or irregular shape. Accordingly, the terms "dome" or "domed," as used herein, are not limited to a circular dome, as it may cover any convex structure.

Figure 7:
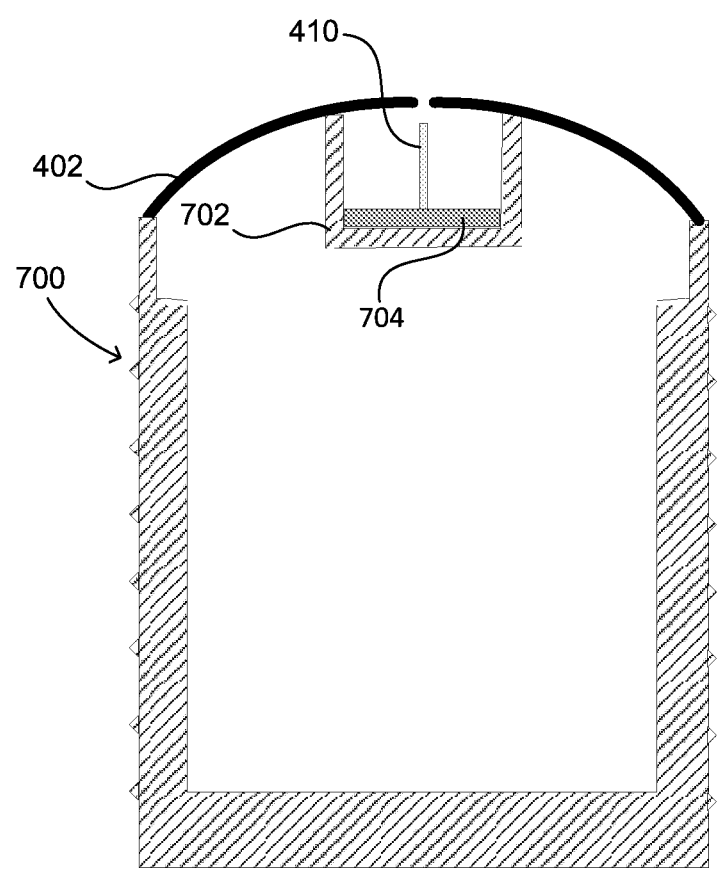
FIG. 7 is a cross-sectional view of an alternative lancet in accordance with one aspect of the disclosure.
Figure 8:
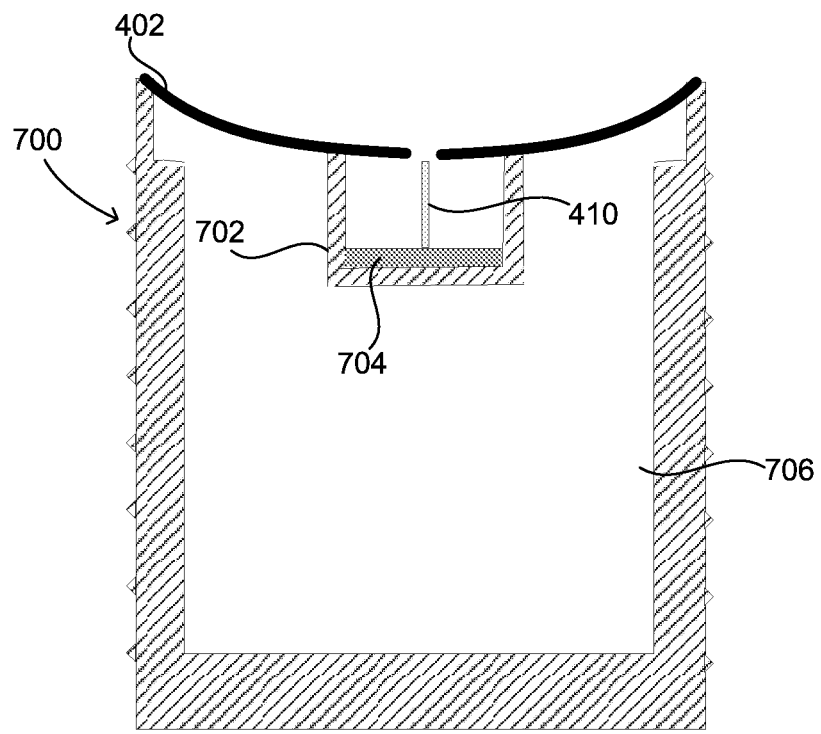
FIG. 8 is a cross-sectional view of the alternative lancet in accordance with another aspect of the disclosure.
Figure 9:
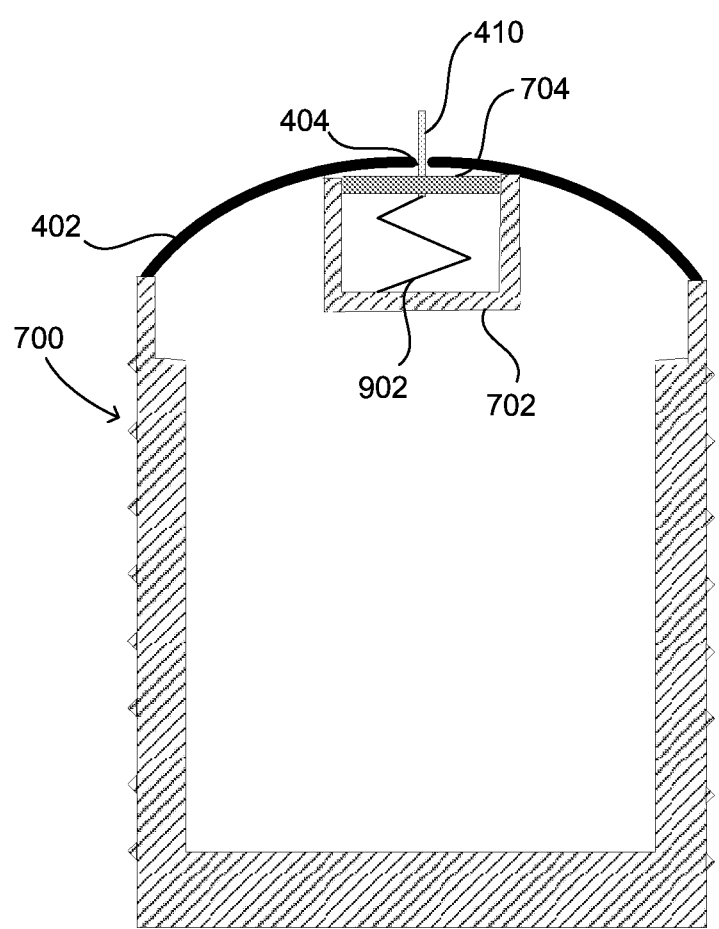
FIG. 9 is a cross-sectional view of the alternative lancet in accordance with yet another aspect of the disclosure.

FIGS. 7-9 show an alternative embodiment of a lancet assembly. As seen in FIG. 7, lancet assembly 700 includes needle 410 that may be contained within a cartridge 702, which is attached to snap lid 402. In addition, needle 410 may be connected to a movable stand 704 that is capable of moving within cartridge 702 in a direction parallel to the axis of needle 410.

FIG. 8 shows lancet assembly 700 of FIG. 7 when it is in a depressed state. As set forth above, snap lid 402 may enter the depressed state when a user presses down on snap lid 402 with sufficient force. In entering the depressed state, snap lid 402 will move into cavity 706 of lancet assembly 700, causing cartridge 702 to move in the same manner. Snap lid 402 may be configured so that the depressed state shown in FIG. 8 is not stable. Accordingly, once the user reduces the force applied to snap lid 402 below a particular threshold level, snap lid 402 will quickly return to the stable position shown in FIG. 7.

FIG. 9 shows lancet assembly 700 when snap lid 402 has been released from the depressed state. In particular, snap lid 402 will travel out of cavity 706, as will cartridge 702. In accordance with one aspect of the embodiment, cartridge 702 may travel with sufficient acceleration and deceleration so as to cause needle 410 and moveable stand 704 to move upward within cartridge 702, thereby causing needle 410 to protrude from aperture 404 of snap lid 402. Moveable stand 704 may be of a particularly dense material, so as to increase the momentum of the needle 410 and stand 704, as they move within cartridge 702. In this way, needle 410 may pierce the user's finger when the user ceases to apply a sufficient force against snap lid 402, as snap lid 402 quickly returns to the non-depressed state.

As shown in FIG. 9, a spring 902 may be connected to moveable stand 704 and cartridge 702. Spring 902 may be arranged so that it will be stretched when stand 704 moves up within cartridge 702. Accordingly, spring 902 will pull stand 704 down from the position shown in FIG. 9, so that needle 410 and stand 704 return to their original positions shown in FIG. 7. Alternatively, spring 902 may be arranged between snap lid 402 and stand 704, so as to push stand 704 down within cartridge 702.

Figure 10:
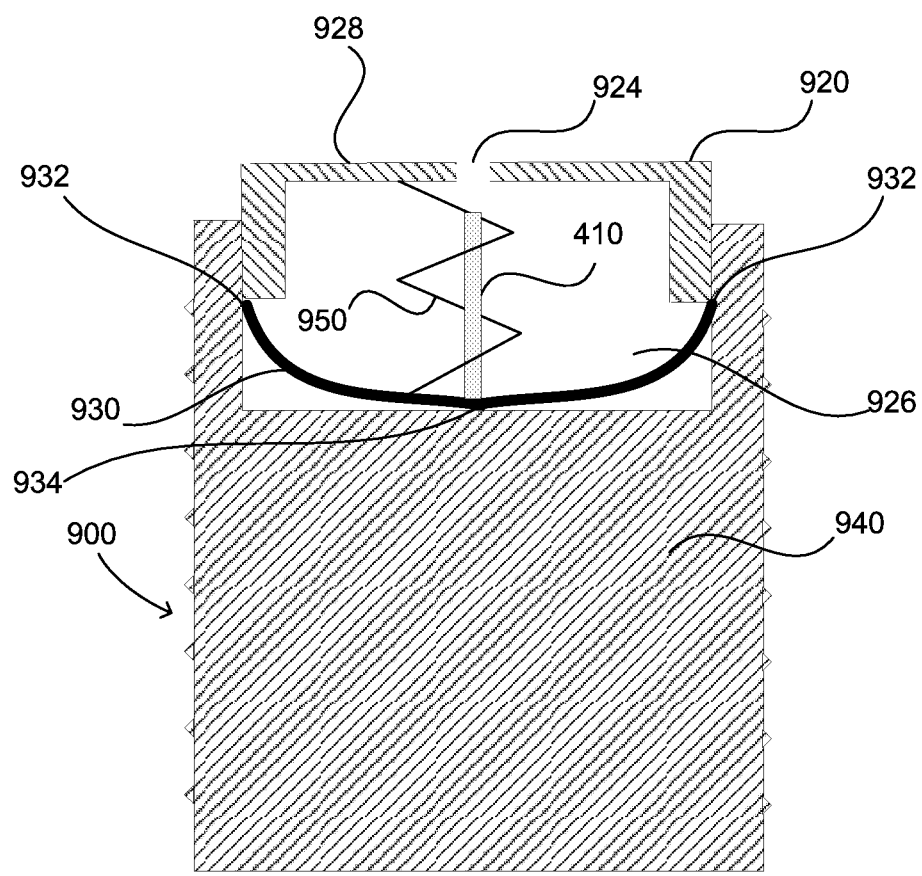
FIG. 10 is a cross-sectional view of yet another alternative lancet in accordance with one aspect of the disclosure.
Figure 11:
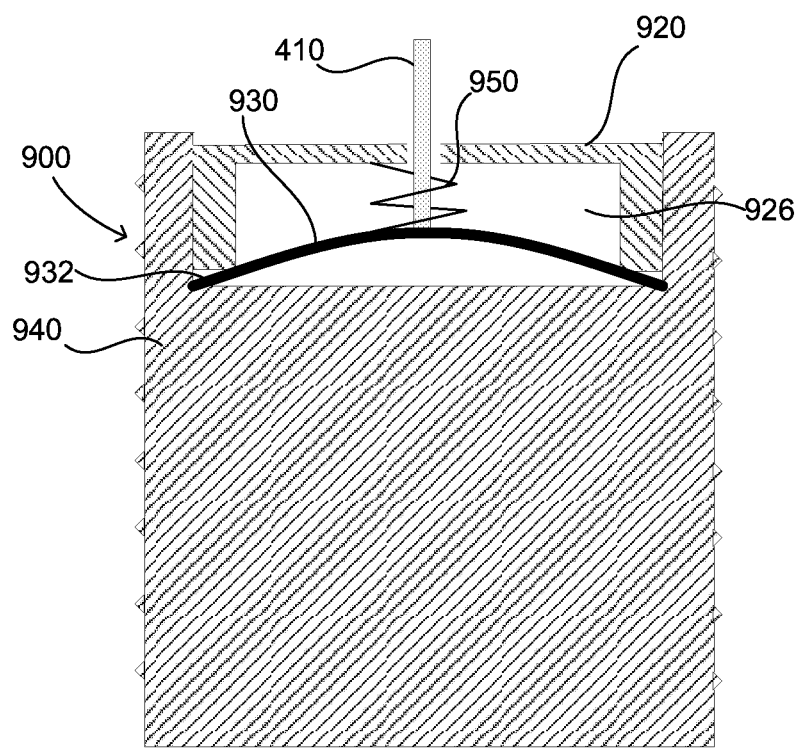
FIG. 11 is a cross-sectional view of the alternative lancet in accordance with one aspect of the disclosure.

FIGS. 10-11 show another embodiment of a lancet assembly. Lancet assembly 900 contains a button 920 and a snap dome 930. Button 920 may have a top surface 928 that is exposed from base 940. Snap dome 930 may have a similar shape and design as described above for snap lid 402 shown in FIGS. 2-9, although it will be arranged in a different manner from the snap lid 402. As seen in FIG. 10, snap dome 930 is arranged within cavity 926 of base 940 so that it is inverted compared to snap lid 402 of FIG. 5. In addition, the edges 932 of snap dome lid 930 are not connected to base 940, although edges 932 may be in contact with base 940. The edges 932 of snap dome 930 may also be in contact with button 920, as shown in FIG. 10. In addition, needle 410 may be connected to the center 934 of snap dome 930, so that needle 410 will move in correspondence with the movement of center 934.

Both button 920 and edges 932 of snap dome 930 are able to move with respect to base 940 in the direction parallel to the axis of needle 410. For example, a user may press down on button 920 so as to cause button 920 to move further into cavity 926, as shown in FIG. 11. As button 920 moves into cavity 926, button 920 will press down on the edge 932 of snap dome 930, so as to force it from the stable state shown in FIG. 10, to a non-stable state shown in FIG. 11. Upon snap dome 930 entering the non-stable state, center 934 of snap dome 930 will move up toward button 920. In turn, this causes needle 410 to move up toward button 920 and through aperture 924 of button 920.

Snap dome 930 may be designed so that the transition from the stable state of FIG. 10 to the non-stable state of FIG. 11 occurs quickly once the user presses down on button 920 with sufficient force. In this way, needle 410 will pierce the finger of the user, as snap dome 930 quickly moves from the stable state to the non-stable state.

Once the user ceases to apply pressure on button 920, snap dome 930 will return to the stable state, causing needle 410 to retract back into cavity 926. As shown in FIGS. 10 and 11, snap dome 930 may be connected to a spring 950. Spring 950 may be arranged between snap dome 930 and button 920 so that it is compressed when snap dome 930 enters the non-stable state. The compression of spring 950 may then assist snap dome 930 in returning to its stable state by pushing the center 934 of snap dome 930 toward the bottom of cavity 926.

Although, this disclosure uses examples of lancing devices, it will be recognized that the features and benefits of the overall construction described herein are applicable to other articles. Also, it would be realized by those skilled in the art that various modifications, alterations, and adaptations can be made to the disclosed embodiments without departing from the spirit and scope of the disclosed features. Numerous characteristics and advantages have been set forth in the foregoing description, together with details of structures and functions of the present invention. The foregoing description and disclosure, however, is illustrative only, and change may be made in arrangement and details, within the principle of the invention to the full extent indicated by the broad general meaning of the terms in which the appended claims are expressed.

Alternative Embodiment A

A lancet device comprising:
a base;
a needle having a tip and having a position relative to the base;
a domed surface having an aperture, the domed surface being arranged in a first configuration relative to the base so as to create a cavity in which at least a portion of the needle resides; and
wherein when a sufficient force is applied to the domed surface, the domed surface transitions from the first configuration to a second configuration in which the tip of the needle protrudes from the aperture of the domed surface.

Alternative Embodiment B

The lancet device of embodiment A, wherein the position of the needle relative to the base does not change during the transition of the domed surface from the first configuration to the second configuration.

Alternative Embodiment C

The lancet device of embodiment A, wherein the domed surface comprises a flexible material; and
wherein the transition from the first configuration to the second configuration includes bending the domed surface.

Alternative Embodiment D

The lancet device of embodiment A, wherein when the force ceases to be applied, the domed surface automatically returns to the first configuration.

Alternative Embodiment E

The lancet device of embodiment A, wherein the position of the needle relative to the base may be altered prior to application of force to the domed surface.

Alternative Embodiment F

The lancet device of embodiment A, wherein the domed surface comprises a middle portion and an outer portion, wherein the outer portion is attached to the base, and wherein the force is applied to the middle portion of the domed surface.

Alternative Embodiment G

The lancet device of embodiment A, wherein a user's finger applies the force to the domed surface, and wherein the protrusion of the tip through the aperture of the domed surface pierces the user's finger so as to draw blood.

Alternative Embodiment H

The lancet device of embodiment A, further comprising:
a main body;

an endcap extending from the main body;
wherein the base is placed within the endcap so that the domed surface is exposed.

Alternative Embodiment I

A lancet device comprising:
a base;
a needle having a tip;
a cartridge in which the needle resides, the cartridge being configured so as to allow the needle to move along the axis of the needle relative to the cartridge;
a domed surface having an aperture, the domed surface being connected to the cartridge and being arranged in a first configuration relative to the base so as to create a cavity in which at least a portion of the cartridge resides;
wherein when a sufficient force is applied to the domed surface, the domed surface transitions from the first configuration to a second configuration;
wherein when the force ceases to be applied, the domed surface returns to the first configuration; and
wherein the domed surface returning to the first configuration causes the needle to move relative to the cartridge so as to allow the tip of the needle to protrude from the aperture of the domed surface.

Alternative Embodiment J

The lancet device of embodiment I, further comprising a stand that is connected to the needle and is configured to move along the axis of the needle relative to the cartridge.

Alternative Embodiment K

The lancet device of embodiment J, further comprising a spring, the spring being arranged within the cartridge so as to cause the needle to return to a position in which the tip of the needle is not protruding through the aperture of the domed surface.

Alternative Embodiment L

The lancet device of embodiment I, wherein the domed surface comprises a flexible material; and
wherein the transition from the first configuration to the second configuration includes bending the domed surface.

Alternative Embodiment M

The lancet device of embodiment I, wherein a user's finger applies the force to the domed surface, and wherein the protrusion of the tip through the aperture of the domed surface pierces the user's finger so as to draw blood.

Alternative Embodiment N

The lancet device of embodiment I, further comprising:
a main body;
an endcap extending from the main body;
wherein the base is placed within the endcap so that the domed surface is exposed.

Alternative Embodiment O

A lancet device comprising:
a base;
a needle having a tip;
a button having an aperture, the button being arranged within the base so that it may move parallel to the axis of the needle, the button having a top surface that is exposed from the base;
a flexible structure having a middle portion and an outer portion, the flexible structure being arranged relative to the button in a first configuration so as to create a cavity in which the needle resides;
wherein when a sufficient force is applied to the top surface of the button, the button will apply force on the outer portion of the flexible structure, causing the flexible structure to transition from the first configuration to a second configuration in which the tip of the needle protrudes from the aperture of the button.

Alternative Embodiment P

The lancet device of embodiment O, further comprising a spring, the spring being arranged between the flexible surface and the button so that it will be compressed when the flexible structure is in the second configuration.

Alternative Embodiment Q

The lancet device of embodiment O, wherein the transition from the first configuration to the second configuration includes bending the flexible structure.

Alternative Embodiment R

The lancet device of embodiment O, wherein a user's finger applies the force to the top surface of the button, and wherein the protrusion of the tip through the aperture of the button pierces the user's finger so as to draw blood.

Alternative Embodiment S

The lancet device of embodiment O, further comprising:
a main body;
an endcap extending from the main body;
wherein the base is placed within the endcap so that the top surface of the button is exposed.

What is claimed is:
1. A lancet device comprising:
a base;
a needle having a tip and a longitudinal axis;
a cartridge in which the needle resides, the cartridge configured to allow the needle to move along the longitudinal axis of the needle relative to the base;
a flexible structure configured to interface with a user and having an aperture, the flexible structure configured to move from a rest state to a use state in response to an applied force by the user;
wherein:
in response to the applied force by the user, the flexible structure is configured to transition from the rest state to the use state, wherein the flexible structure is configured to invert while in the use state;
in response to the force ceasing to be applied, the flexible structure is configured to transition from the use state to the rest state;
and in response to the flexible structure transitioning from the use state to the rest state, the needle is configured to move relative to the base such that the tip of the needle protrudes from the aperture of the flexible structure.

2. The lancet device of claim 1, further comprising a stand connected to the needle inside the cartridge, the stand configured to move parallel to the longitudinal axis of the needle relative to the base.

3. The lancet device of claim 1, further comprising a spring, wherein the spring in a compressed state is configured to position the needle such that the tip of the needle is not protruding through the aperture of the flexible structure.

4. The lancet device of claim 1, further comprising a spring, wherein the spring in an uncompressed state is configured to position the needle such that the tip of the needle protrudes through the aperture of the flexible structure.

5. The lancet device of claim 1, wherein the flexible structure comprises a domed surface, and wherein the domed surface is configured to invert when transitioning between the rest state and the use state.

6. The lancet device of claim 1, further comprising:
a main body;
and an endcap extending from the main body;
wherein the endcap is attached to the base such that the flexible structure is exposed.

7. The lancet device of claim 6, wherein the base has external threads configured to allow the base to be adjustably positioned within the endcap.

8. The lancet device of claim 6, wherein the main body comprises an upper portion and a lower portion mated to the upper portion.

9. The lancet device of claim 1, wherein the base has a cavity configured to receive the cartridge when the flexible structure inverts during the transition between the rest state and use state.

10. The lancet device of claim 1, wherein in response to the applying of the force to the flexible structure by a finger of the user and then ceasing to apply the force, the protrusion of the tip of the needle through the aperture of the flexible structure is configured to pierce the finger of the user so as to draw blood.

11. A lancet device comprising:
a base;
a needle having a tip and a longitudinal axis;
an actuation button, arranged within the base such that the button is movable parallel to the longitudinal axis of the needle, wherein the actuation button is movable from a rest state to a use state;
a resilient member to provide a resistive force against the actuation button;
and a flexible structure, interfacing with the actuation button and configured to move from the rest state to the use state in response to an actuation of the actuation button,
wherein, when the actuation button is in the rest state, responsive to the actuation of the actuation button with an applied force, the actuation button is configured to overcome the resistive force of the resilient member to thereby move the flexible structure from the rest state to the use state,
wherein, when in the use state, the flexible structure is configured to invert and the tip of the needle is configured to protrude from an aperture in the actuation button.

12. The lancet device of claim 11, wherein the resilient member is a spring, the spring uncompressed when the flexible structure is in the rest state.

13. The lancet device of claim 11, wherein the resilient member is a spring, the spring configured to be compressed when the flexible structure transitions to the use state.

14. The lancet device of claim 11, wherein the transition from the rest state to the use state includes bending the flexible structure.

15. The lancet device of claim 11, wherein in response to a user's finger applying the force to a top surface of the button, the protrusion of the tip of the needle through the aperture of the button is configured to pierce the user's finger so as to draw blood.

16. The lancet device of claim 11, wherein the flexible structure has a domed shape.

17. The lancet device of claim 11, wherein the needle is connected to a center of the flexible structure.

18. The lancet device of claim 11, further comprising:
a main body;
and an endcap extending from the main body;
wherein the endcap is attached to the main body such that the top surface of the button is exposed.

19. The lancet device of claim 18, wherein the base has external threads configured to allow the base to be adjustably positioned within the endcap.

20. The lancet device of claim 18, wherein the main body comprises an upper portion and a lower portion mated to the upper portion.

* * * * *